United States Patent
Perlo et al.

(10) Patent No.: US 6,939,332 B2
(45) Date of Patent: Sep. 6, 2005

(54) CONTROLLED SHUTTER, WITH VARIABLE SECTION

(75) Inventors: Piero Perlo, Orbassano (IT); Gianfranco Innocenti, Orbassano (IT); Stefano Alacqua, Orbassano (IT)

(73) Assignee: C.R.F. Societa Consortile per Azioni, Orbassano (IT)

(*) Notice: Subject to any disclaimer, the term of this patent is extended or adjusted under 35 U.S.C. 154(b) by 404 days.

(21) Appl. No.: 10/102,683

(22) Filed: Mar. 22, 2002

(65) Prior Publication Data

US 2002/0138052 A1 Sep. 26, 2002

(30) Foreign Application Priority Data

Mar. 23, 2001 (IT) .................................... TO2001A0274

(51) Int. Cl.$^7$ ................................................. A61F 5/44
(52) U.S. Cl. ...................... 604/328; 604/348; 604/355
(58) Field of Search ................................ 604/327–328, 604/332–345, 348, 355

(56) References Cited

U.S. PATENT DOCUMENTS

| | | | | |
|---|---|---|---|---|
| 3,570,488 A | * | 3/1971 | Diskin et al. | 604/31 |
| 3,675,653 A | * | 7/1972 | Crowley et al. | 604/120 |
| 4,482,347 A | * | 11/1984 | Borsanyi | 604/153 |
| 5,342,583 A | * | 8/1994 | Son | 422/107 |
| 5,356,400 A | * | 10/1994 | Temple | 604/356 |
| 6,527,755 B1 | * | 3/2003 | Salama | 604/348 |

* cited by examiner

Primary Examiner—Larry I. Schwartz
Assistant Examiner—C. Lynne Anderson
(74) Attorney, Agent, or Firm—Sughrue Mion, PLLC

(57) ABSTRACT

The object of the invention is a collection device that can be carried by disabled persons, comprising a section of duct, destined to be connected to the rectum of the person, an expansible container, connected to said section of duct, and a shutter device interposed in the aforesaid section of duct and controlled by actuator means, for example shape-memory or electromagnetic means, activated by the signal of a sensor.

6 Claims, 2 Drawing Sheets

CONTROLLED SHUTTER, WITH VARIABLE SECTION

BACKGROUND OF THE INVENTION

The present invention relates to a device for the collection of faeces, which can be carried by disabled persons.

SUMMARY OF THE INVENTION

The object of the present invention is to produce a device of the type indicated above that is relatively simple, functional, small in size and low cost.

In view of attaining this object, the invention relates to a collection device comprising:

- a section of duct, destined to be connected to the rectum of the disabled person,
- an expansible container, connected to said section of duct, and destined to collect the faeces, and
- a shutter device interposed in the aforesaid section of duct and controlled by actuator means.

The expansible container is preferably of the disposable type and is connected to the aforesaid section of duct in a disconnectible manner.

The device according to the invention can have a sensor of the evacuation stimulus or alternatively a sensor of the flow of material in the aforesaid section of duct, and electronic control means suitable to process the electric signals emitted by said sensors and to consequently control opening and closing of the shutter device by means of the aforesaid actuator means.

The device may include a battery-operated remote electric supply system, which can be carried, for example, in the belt by the user, or alternatively a supply system of the type with mini-batteries.

According to a further characteristic, between the actuator means of the shutter device and the container a membrane to withhold evacuated gases can be interposed, provided for example with a layer of activated carbon, also acting as a filter.

In a possible embodiment, the actuator means of the shutter device are of the type with shape memory. Shape-memory actuators exploit the property of some materials, typically nickel and titanium alloys, which are subject to contraction when heated to a transition temperature. These actuators are characterized in that they are very small in size, require a very low supply power and are very reliable and efficient. The invention can be utilized in any case with any type of actuator, such as an electromagnetic actuator.

The shutter device, which is part of the device according to the invention, can also be activated manually, with a cable control and preferable a radio-frequency control. An additional device with a peristaltic effect may also be provided, suitable to generate a wave activation control travelling along the section of duct.

The structure and arrangement of the shutter device may in any case be of any type. An alternative embodiment is composed of a cylindrical section of duct, the bases of which are made to rotate in opposite directions so as to create torsion of the aforesaid section of duct which causes blocking. This result may be obtained by means of an annular planar motor or by means of shape-memory wires.

Another embodiment of the shutter comprises a port structure, or an expansible ring structure.

BRIEF DESCRIPTION OF THE DRAWINGS

Further characteristics and advantages of the invention shall become apparent in the description below with reference to the accompanying drawings, provided purely as a non-limiting example, in which.

DETAILED DESCRIPTION OF THE INVENTION

Figure 1:
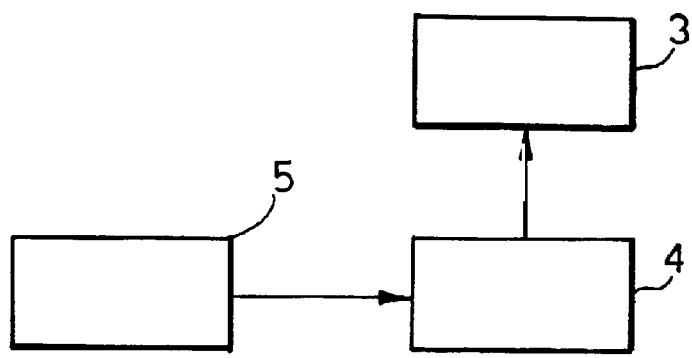
FIG. 1 shows a block diagram of the control system of the device according to the invention.
Figure 4:
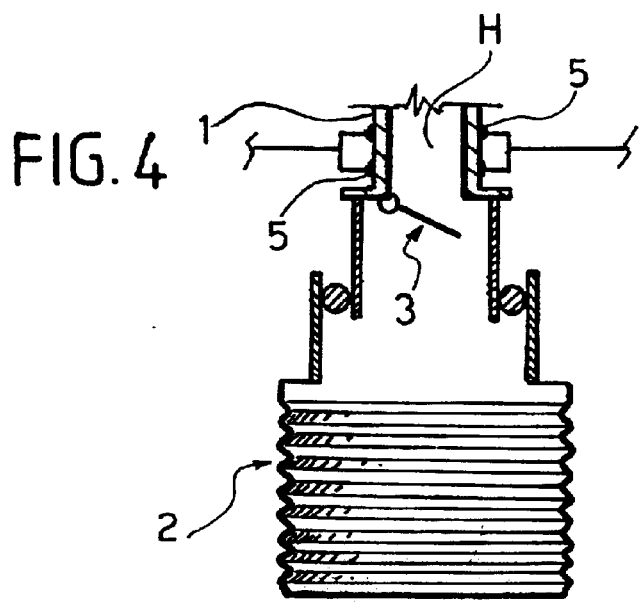
FIG. 4 shows another arrangement of the shutter according to the invention.

FIG. 4 of the accompanying drawings shows an example of embodiment of the device according to the invention, comprising a section of duct 1, destined to be connected to the rectum of a disabled person. The section of duct 1 is connected, preferably in a disconnectible manner, to an expansible bag 2, preferably of the disposable type, destined to collect the faeces, by means of a shutter device 3 controlled by an actuator of any type (for example shape-memory) activated by the signal emitted by one or more sensors 5 associated with the wall of the duct 1 for the purpose of signalling the passage of faeces. FIG. 4 shows the shutter device 3 in a suitable position if this device is activated manually. The shutter 3 may nonetheless be fitted at the section H, in which case it is controlled by actuator means 4 (FIG. 1) following the signal sent by sensor means 5, for example of the type already described composed of electrodes incorporated in the wall of the duct 1, suitable to detect an evacuation stimulus or alternatively a flow of material through the duct.

According to the invention, the shutter device is controlled by an actuator of any type, such as an electromagnetic actuator or preferably a shape-memory actuator.

Figure 2:
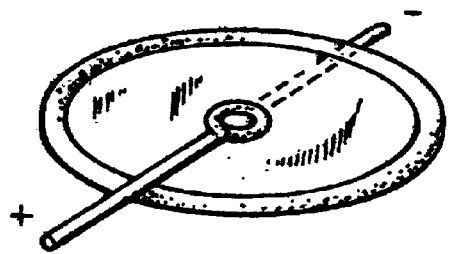
FIGS. 2, 3 show a first embodiment of the shutter according to the invention in two different operating conditions.
Figure 3:
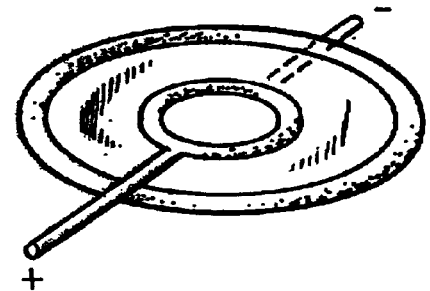

FIGS. 2, 3 show, in the closed condition and in the open condition, a shutter composed of an expansible annular membrane, activated in opening by shape-memory tie-rods.

Figure 5:
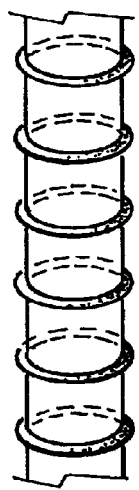
FIGS. 5, 6 show two possible embodiments of peristaltic devices utilizable according to the invention.
Figure 6:
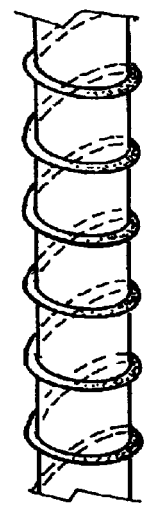

FIGS. 5, 6 show two alternative embodiments of devices with peristaltic effect capable of generating a wave activation control travelling along the duct, to favour advance of waste material in the duct. In the case in FIG. 5, shape-memory rings are provided, which are heated in succession by the passage of an electric current, so that they contract in sequence. In FIG. 6 the rings are replaced by a spiral wire, the successive portions of which are heated in sequence.

Figure 7:
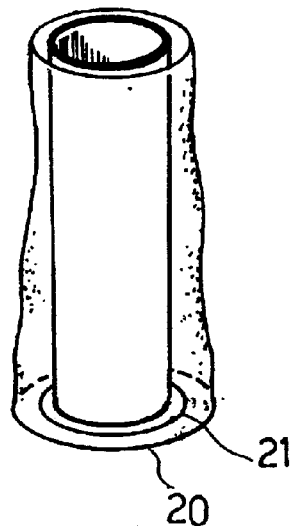
FIGS. 7, 8 show a further embodiment of the shutter according to the invention in two different operating conditions.
Figure 8:
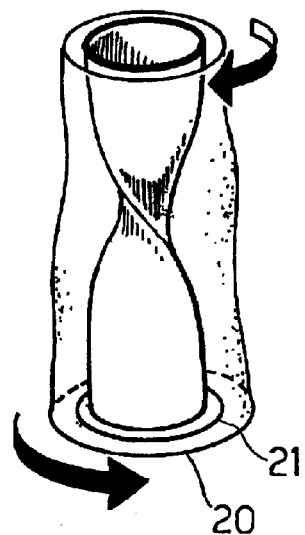

Lastly, FIGS. 7, 8 show an alternative embodiment of shutter, in which a cylindrical section of duct has end bases that are rotated in opposite directions to generate torsion that determines blocking of the duct. This deformation can be obtained by connecting one end to a fixed ring and the other end to a ring forming a rotor of a planar electric motor, including a concentric and coplanar stator 20 and rotor 21.

With reference to FIG. 4, the section of duct 1 that is connected to the rectum of the disabled person has a stretch in permeable porous material, to consent transpiration.

What is claimed is:

1. Collection device comprising:
    a section of duct, destined to be connected to the rectum of a disabled person,
    an expansible container, connected to said section of the duct, and destined to collect faeces, and a shutter device interposed in the aforesaid section of duct and controlled by actuator means, wherein the collection device comprises a sensor of the evacuation stimulus or alternatively a sensor of the flow of material in the aforesaid section of the duct, and electronic control means suitable to process the electric signals emitted by said sensors and to consequently control opening and closing of the shutter device by means of the aforesaid actuator means, and wherein between the actuator means of the shutter device and the container a membrane to withhold evacuated gases can be interposed, which may be provided with a layer of activated carbon, acting as a filter.

2. Collection device comprising:

a section of duct, destined to be connected to the rectum of a disabled person, an expansible container, connected to said section of the duct, and destined to collect faeces, and a shutter device interposed in the aforesaid section of duct and controlled by actuator means, wherein the collection device comprises a sensor of the evacuation stimulus or alternatively a sensor of the flow of material in the aforesaid section of the duct, and electronic control means suitable to process the electric signals emitted by said sensors and to consequently control opening and closing of the shutter device by means of the aforesaid actuator means, and wherein the collection device comprises an additional device with a peristaltic effect, suitable to generate a wave activation control traveling along the section duct, and wherein said additional device with a peristaltic effect comprises shape-memory sections applied along the section of duct and suitable to contract in succession.

3. Collection device comprising:

a section of duct, destined to be connected to the rectum of a disabled person, an expansible container, connected to said section of the duct, and destined to collect faeces, and a shutter device interposed in the aforesaid section of duct and controlled by actuator means, wherein the collection device comprises a sensor of the evacuation stimulus or alternatively a sensor of the flow of material in the aforesaid section of the duct, and electronic control means suitable to process the electric signals emitted by said sensors and to consequently control opening and closing of the shutter device by means of the aforesaid actuator means, and wherein the collection device comprises a cylindrical section of duct, the bases of which are made to rotate in opposite directions, for example by means of a planar electric motor or shape-memory actuators, so as to create torsion of the aforesaid section of duct which causes blocking.

4. Collection device comprising:

a section of duct, destined to be connected to the rectum of a disabled person, an expansible container, connected to said section of the duct, and destined to collect faeces, and a shutter device interposed in the aforesaid section of duct and controlled by actuator means, wherein the collection device comprises a sensor of the evacuation stimulus or alternatively a sensor of the flow of material in the aforesaid section of the duct, and electronic control means suitable to process the electric signals emitted by said sensors and to consequently control opening and closing of the shutter device by means of the aforesaid actuator means, and wherein said sensor comprises an expansible annular membrane controlled by shape-memory tie-rods.

5. Collection device comprising:

a section of duct, destined to be connected to the rectum of a disabled person, an expansible container, connected to said section of the duct, and destined to collect faeces, and a shutter device interposed in the aforesaid section of duct and controlled by actuator means, wherein said actuator means are comprised of shape-memory actuators.

6. Collection device comprising:

a section of duct, destined to be connected to the rectum of a disabled person, a shutter device interposed in the aforesaid section of duct and controlled by actuator means, wherein said actuator means are comprised of shape-memory actuators.

* * * * *